United States Patent
Grell et al.

(10) Patent No.: US 6,924,357 B2
(45) Date of Patent: Aug. 2, 2005

(54) LIPID BINDING PROTEIN 4

(75) Inventors: Matthias Grell, Darmstadt (DE); Klaus Dücker, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 469 days.

(21) Appl. No.: 10/257,637

(22) PCT Filed: Apr. 11, 2001

(86) PCT No.: PCT/EP01/04170

§ 371 (c)(1),
(2), (4) Date: Oct. 16, 2002

(87) PCT Pub. No.: WO01/79269

PCT Pub. Date: Oct. 25, 2001

(65) Prior Publication Data

US 2003/0124582 A1 Jul. 3, 2003

(30) Foreign Application Priority Data

Apr. 18, 2000 (EP) .............................................. 00107995

(51) Int. Cl.⁷ .............................................. C07K 14/47
(52) U.S. Cl. ...................................................... 530/350
(58) Field of Search ........................................... 530/350

(56) References Cited

PUBLICATIONS

Dear, T.N., et al: "Novel genes for potential ligand–binding proteins in subregions of the olfactory mucosa"; The Embo Journal vol. 10, No. 10, 1991, pp. 2813–2819; XP002181718 p. 2816; figure 3.

Database EMBL Online! IDi HS187217; Accession No.: H65167. Oct. 20, 1995 "yu64g01.ri Weizmann olfactory epithelium *Homo sapiens* cDNA clone Image:238608 5' similar to SP:S17447 S17447 Probable Ligand–Binding Protein RY2G5—;, mRNA sequence" XP002181719 abstract.

*Primary Examiner*—Robert A. Wax
(74) *Attorney, Agent, or Firm*—Millen, White, Zelano & Branigan, P.C.

(57) ABSTRACT

Lipid Binding Protein 4 polypeptides and polynucleotides and methods for producing such polypeptides by recombinant techniques are disclosed. Also disclosed are methods for utilizing Lipid Binding Protein 4 polypeptides and polynucleotides in diagnostic assays.

10 Claims, No Drawings

SEQUENCE LISTING

<160> NUMBER OF SEQ ID NOS: 4

<210> SEQ ID NO 1
<211> LENGTH: 1842
<212> TYPE: DNA
<213> ORGANISM: Homo sapiens
<220> FEATURE:
<221> NAME/KEY: CDS
<222> LOCATION: (1)..(1842)

<400> SEQUENCE: 1

```
atg tgg atg gcc tgg tgt gtg gct gcg ctg tct gtg gtg gct gtg tgt      48
Met Trp Met Ala Trp Cys Val Ala Ala Leu Ser Val Val Ala Val Cys
```

-continued

| | | | | | | | | | | | | | | | | |
|---|---|---|---|---|---|---|---|---|---|---|---|---|---|---|---|---|
| 1 | | | | 5 | | | | | 10 | | | | | 15 | | |

```
ggc acc agc cac gag aca aac acg gtc ctc agg gtg acg aaa gat gtg      96
Gly Thr Ser His Glu Thr Asn Thr Val Leu Arg Val Thr Lys Asp Val
             20                  25                  30 ttg agc aat gcc att tca ggc atg ctg cag caa agt gat gct ctc cac     144
Leu Ser Asn Ala Ile Ser Gly Met Leu Gln Gln Ser Asp Ala Leu His
         35                  40                  45 tcg gcc ctg aga gag gtg ccc ttg ggt gtt ggt gat att ccc tac aat     192
Ser Ala Leu Arg Glu Val Pro Leu Gly Val Gly Asp Ile Pro Tyr Asn
     50                  55                  60 gac ttc cat gtc cga gga ccc ccc cca gta tat acc aac ggc aaa aaa     240
Asp Phe His Val Arg Gly Pro Pro Pro Val Tyr Thr Asn Gly Lys Lys
 65                  70                  75                  80 ctt gat ggt att tac cag tat ggt cac att gag acc aac gac aac act     288
Leu Asp Gly Ile Tyr Gln Tyr Gly His Ile Glu Thr Asn Asp Asn Thr
                 85                  90                  95 gct cag ctg ggg ggc aaa tac cga tat ggt gag atc ctt gag tcc gag     336
Ala Gln Leu Gly Gly Lys Tyr Arg Tyr Gly Glu Ile Leu Glu Ser Glu
             100                 105                 110 gga agc atc agg gac ctc cga aac agt ggc tat cgc agt gcc gag aat     384
Gly Ser Ile Arg Asp Leu Arg Asn Ser Gly Tyr Arg Ser Ala Glu Asn
         115                 120                 125 gca tat gga ggc cac agg ggc ctc ggg cga tac agg gca gca cct gtg     432
Ala Tyr Gly Gly His Arg Gly Leu Gly Arg Tyr Arg Ala Ala Pro Val
     130                 135                 140 ggc agg ctt cac cgg cga gag ctg cag cct gga gaa atc cca cct gga     480
Gly Arg Leu His Arg Arg Glu Leu Gln Pro Gly Glu Ile Pro Pro Gly
145                 150                 155                 160 gtt gcc act ggg gcg gtg ggc cca ggt ggt ttg ctg ggc act gga ggc     528
Val Ala Thr Gly Ala Val Gly Pro Gly Gly Leu Leu Gly Thr Gly Gly
                 165                 170                 175 atg ctg gca gct gat ggc atc ctc gca ggc caa ggt ggc ctg ctc ggc     576
Met Leu Ala Ala Asp Gly Ile Leu Ala Gly Gln Gly Gly Leu Leu Gly
             180                 185                 190 gga ggt ggt ctc ctt ggt gat gga gga ctt ctt gga gga ggg ggt gtc     624
Gly Gly Gly Leu Leu Gly Asp Gly Gly Leu Leu Gly Gly Gly Gly Val
         195                 200                 205 ctg ggc gtg ctc ggc gag ggt ggc atc ctc agc act gtg caa ggc atc     672
Leu Gly Val Leu Gly Glu Gly Gly Ile Leu Ser Thr Val Gln Gly Ile
     210                 215                 220 acg ggg ctg cgt atc gtg gag ctg acc ctc cct cgg gtg tcc gtg cgg     720
Thr Gly Leu Arg Ile Val Glu Leu Thr Leu Pro Arg Val Ser Val Arg
225                 230                 235                 240 ctc ctg ccc ggc gtg ggt gtc tac ctg agc ttg tac acc cgt gtg gcc     768
Leu Leu Pro Gly Val Gly Val Tyr Leu Ser Leu Tyr Thr Arg Val Ala
                 245                 250                 255 atc aac ggg aag agt ctt att ggc ttc ctg gac gtc gca gta gaa gtg     816
Ile Asn Gly Lys Ser Leu Ile Gly Phe Leu Asp Val Ala Val Glu Val
             260                 265                 270 aac atc aca gcc aag gtc cgg ctg acc atg gac cgc acg ggt tat cct     864
Asn Ile Thr Ala Lys Val Arg Leu Thr Met Asp Arg Thr Gly Tyr Pro
         275                 280                 285 cgg ctg gtc att gag cga tgt gac acc ctc cta ggg ggc atc aaa gtc     912
Arg Leu Val Ile Glu Arg Cys Asp Thr Leu Leu Gly Gly Ile Lys Val
     290                 295                 300 aag ctg ctg cga ggg ctt ctc ccc aat ctc gtg gac aat tta gtg acc     960
Lys Leu Leu Arg Gly Leu Leu Pro Asn Leu Val Asp Asn Leu Val Thr
305                 310                 315                 320 cga gtc ctg gcc gac gtc ctc cct gac ttg ctc tgc ccc atc gtg gat    1008
```

```
Arg Val Leu Ala Asp Val Leu Pro Asp Leu Leu Cys Pro Ile Val Asp
            325                 330                 335 gtg gtg ctg ggt ctt gtc aat gac cag ctg ggc ctc gtg gat tct ctg      1056
Val Val Leu Gly Leu Val Asn Asp Gln Leu Gly Leu Val Asp Ser Leu
            340                 345                 350 att cct ctg ggg ata ttg gga agt gtc cag tac acc ttc tcc agc ctc      1104
Ile Pro Leu Gly Ile Leu Gly Ser Val Gln Tyr Thr Phe Ser Ser Leu
            355                 360                 365 ccg ctt gtg acc ggg gaa ttc ctg gag ctg gac ctc aac acg ctg gtt      1152
Pro Leu Val Thr Gly Glu Phe Leu Glu Leu Asp Leu Asn Thr Leu Val
        370                 375                 380 ggg gag gct gga gga gga ctc atc gac tac cca ttg ggg tgg cca gct      1200
Gly Glu Ala Gly Gly Gly Leu Ile Asp Tyr Pro Leu Gly Trp Pro Ala
385                 390                 395                 400 gtg tct ccc aag ccg atg cca gag ctg cct ccc atg ggt gac aac acc      1248
Val Ser Pro Lys Pro Met Pro Glu Leu Pro Pro Met Gly Asp Asn Thr
            405                 410                 415 aag tcc cag ctg gcc atg tct gcc aac ttc ctg ggc tca gtg ctg act      1296
Lys Ser Gln Leu Ala Met Ser Ala Asn Phe Leu Gly Ser Val Leu Thr
            420                 425                 430 cta ctg cag aag cag cat gct cta gac ctg gat atc acc aat ggc atg      1344
Leu Leu Gln Lys Gln His Ala Leu Asp Leu Asp Ile Thr Asn Gly Met
            435                 440                 445 ttt gaa gag ctt cct cca ctt acc aca gcc aca ctg gga gcc ctg atc      1392
Phe Glu Glu Leu Pro Pro Leu Thr Thr Ala Thr Leu Gly Ala Leu Ile
        450                 455                 460 ccc aag gtg ttc cag cag tac ccc gag tcc tgc cca ctt atc atc agg      1440
Pro Lys Val Phe Gln Gln Tyr Pro Glu Ser Cys Pro Leu Ile Ile Arg
465                 470                 475                 480 atc cag gtg ctg aac cca cca tct gtg atg ctg cag aag gac aaa gcg      1488
Ile Gln Val Leu Asn Pro Pro Ser Val Met Leu Gln Lys Asp Lys Ala
            485                 490                 495 ctg gtg aag gtg ttg gcc act gcc gag gtc atg gtc tcc cag ccc aaa      1536
Leu Val Lys Val Leu Ala Thr Ala Glu Val Met Val Ser Gln Pro Lys
            500                 505                 510 gac ctg gag act acc atc tgc ctc att gac gtg gac aca gaa ttc ttg      1584
Asp Leu Glu Thr Thr Ile Cys Leu Ile Asp Val Asp Thr Glu Phe Leu
            515                 520                 525 gcc tca ttt tcc aca gaa gga gat aag ctc atg att gat gcc aag ctg      1632
Ala Ser Phe Ser Thr Glu Gly Asp Lys Leu Met Ile Asp Ala Lys Leu
        530                 535                 540 gag aag acc agc ctc aac ctc aga acc tca aac gtg ggc aac ttt gat      1680
Glu Lys Thr Ser Leu Asn Leu Arg Thr Ser Asn Val Gly Asn Phe Asp
545                 550                 555                 560 att ggc ctc atg gag gtg ctg gtg gag aag att ttt gac ctg gca ttc      1728
Ile Gly Leu Met Glu Val Leu Val Glu Lys Ile Phe Asp Leu Ala Phe
            565                 570                 575 atg ccc gca atg aac gct gtg ctg ggt tct ggc gtc cct ctc ccc aaa      1776
Met Pro Ala Met Asn Ala Val Leu Gly Ser Gly Val Pro Leu Pro Lys
            580                 585                 590 atc ctc aac atc gac ttt agc aat gca gac att gac gtg ttg gag gac      1824
Ile Leu Asn Ile Asp Phe Ser Asn Ala Asp Ile Asp Val Leu Glu Asp
            595                 600                 605 ctt ttg gtg ctg agc gca                                              1842
Leu Leu Val Leu Ser Ala
        610

<210> SEQ ID NO 2
<211> LENGTH: 614
<212> TYPE: PRT
```

<213> ORGANISM: Homo sapiens

<400> SEQUENCE: 2

```
Met Trp Met Ala Trp Cys Val Ala Ala Leu Ser Val Ala Val Cys
  1               5                  10                  15

Gly Thr Ser His Glu Thr Asn Thr Val Leu Arg Val Thr Lys Asp Val
                 20                  25                  30

Leu Ser Asn Ala Ile Ser Gly Met Leu Gln Gln Ser Asp Ala Leu His
             35                  40                  45

Ser Ala Leu Arg Glu Val Pro Leu Gly Val Gly Asp Ile Pro Tyr Asn
     50                  55                  60

Asp Phe His Val Arg Gly Pro Pro Val Tyr Thr Asn Gly Lys Lys
 65                  70                  75                  80

Leu Asp Gly Ile Tyr Gln Tyr Gly His Ile Glu Thr Asn Asp Asn Thr
                 85                  90                  95

Ala Gln Leu Gly Gly Lys Tyr Arg Tyr Gly Glu Ile Leu Glu Ser Glu
            100                 105                 110

Gly Ser Ile Arg Asp Leu Arg Asn Ser Gly Tyr Arg Ser Ala Glu Asn
        115                 120                 125

Ala Tyr Gly Gly His Arg Gly Leu Gly Arg Tyr Arg Ala Ala Pro Val
    130                 135                 140

Gly Arg Leu His Arg Arg Glu Leu Gln Pro Gly Glu Ile Pro Pro Gly
145                 150                 155                 160

Val Ala Thr Gly Ala Val Gly Pro Gly Gly Leu Leu Gly Thr Gly Gly
                165                 170                 175

Met Leu Ala Ala Asp Gly Ile Leu Ala Gly Gln Gly Gly Leu Leu Gly
                180                 185                 190

Gly Gly Gly Leu Leu Gly Asp Gly Gly Leu Leu Gly Gly Gly Gly Val
        195                 200                 205

Leu Gly Val Leu Gly Glu Gly Gly Ile Leu Ser Thr Val Gln Gly Ile
    210                 215                 220

Thr Gly Leu Arg Ile Val Glu Leu Thr Leu Pro Arg Val Ser Val Arg
225                 230                 235                 240

Leu Leu Pro Gly Val Gly Val Tyr Leu Ser Leu Tyr Thr Arg Val Ala
                245                 250                 255

Ile Asn Gly Lys Ser Leu Ile Gly Phe Leu Asp Val Ala Val Glu Val
                260                 265                 270

Asn Ile Thr Ala Lys Val Arg Leu Thr Met Asp Arg Thr Gly Tyr Pro
            275                 280                 285

Arg Leu Val Ile Glu Arg Cys Asp Thr Leu Leu Gly Gly Ile Lys Val
    290                 295                 300

Lys Leu Leu Arg Gly Leu Leu Pro Asn Leu Val Asp Asn Leu Val Thr
305                 310                 315                 320

Arg Val Leu Ala Asp Val Leu Pro Asp Leu Leu Cys Pro Ile Val Asp
                325                 330                 335

Val Val Leu Gly Leu Val Asn Asp Gln Leu Gly Leu Val Asp Ser Leu
                340                 345                 350

Ile Pro Leu Gly Ile Leu Gly Ser Val Gln Tyr Thr Phe Ser Ser Leu
            355                 360                 365

Pro Leu Val Thr Gly Glu Phe Leu Glu Leu Asp Leu Asn Thr Leu Val
    370                 375                 380

Gly Glu Ala Gly Gly Gly Leu Ile Asp Tyr Pro Leu Gly Trp Pro Ala
385                 390                 395                 400
```

```
Val Ser Pro Lys Pro Met Pro Glu Leu Pro Pro Met Gly Asp Asn Thr
                405                 410                 415

Lys Ser Gln Leu Ala Met Ser Ala Asn Phe Leu Gly Ser Val Leu Thr
                420                 425                 430

Leu Leu Gln Lys Gln His Ala Leu Asp Leu Asp Ile Thr Asn Gly Met
                435                 440                 445

Phe Glu Glu Leu Pro Pro Leu Thr Thr Ala Thr Leu Gly Ala Leu Ile
450                 455                 460

Pro Lys Val Phe Gln Gln Tyr Pro Glu Ser Cys Pro Leu Ile Ile Arg
465                 470                 475                 480

Ile Gln Val Leu Asn Pro Ser Val Met Leu Gln Lys Asp Lys Ala
                485                 490                 495

Leu Val Lys Val Leu Ala Thr Ala Glu Val Met Val Ser Gln Pro Lys
                500                 505                 510

Asp Leu Glu Thr Thr Ile Cys Leu Ile Asp Val Asp Thr Glu Phe Leu
                515                 520                 525

Ala Ser Phe Ser Thr Glu Gly Asp Lys Leu Met Ile Asp Ala Lys Leu
530                 535                 540

Glu Lys Thr Ser Leu Asn Leu Arg Thr Ser Asn Val Gly Asn Phe Asp
545                 550                 555                 560

Ile Gly Leu Met Glu Val Leu Val Glu Lys Ile Phe Asp Leu Ala Phe
                565                 570                 575

Met Pro Ala Met Asn Ala Val Leu Gly Ser Gly Val Pro Leu Pro Lys
                580                 585                 590

Ile Leu Asn Ile Asp Phe Ser Asn Ala Asp Ile Asp Val Leu Glu Asp
                595                 600                 605

Leu Leu Val Leu Ser Ala
        610

<210> SEQ ID NO 3
<211> LENGTH: 1914
<212> TYPE: DNA
<213> ORGANISM: Homo sapiens
<220> FEATURE:
<221> NAME/KEY: CDS
<222> LOCATION: (1)..(1914)

<400> SEQUENCE: 3 atg tgg atg gcc tgg tgt gtg gct gcg ctg tct gtg gtg gct gtg tgt      48
Met Trp Met Ala Trp Cys Val Ala Ala Leu Ser Val Val Ala Val Cys
 1               5                  10                  15 ggc acc agc cac gag aca aac acg gtc ctc agg gtg acg aaa gat gtg      96
Gly Thr Ser His Glu Thr Asn Thr Val Leu Arg Val Thr Lys Asp Val
                 20                  25                  30 ttg agc aat gcc att tca ggc atg ctg cag caa agt gat gct ctc cac     144
Leu Ser Asn Ala Ile Ser Gly Met Leu Gln Gln Ser Asp Ala Leu His
             35                  40                  45 tcg gcc ctg aga gag gtg ccc ttg ggt aaa gcc cgt ggt gat ggt ggt     192
Ser Ala Leu Arg Glu Val Pro Leu Gly Lys Ala Arg Gly Asp Gly Gly
         50                  55                  60 ggg cct ctc ctg ggc ggt ctg ctt ggt gga agt gga agt gga ggt ggt     240
Gly Pro Leu Leu Gly Gly Leu Leu Gly Gly Ser Gly Ser Gly Gly Gly
 65                  70                  75                  80 gtt ggt gat att ccc tac aat gac ttc cat gtc cga gga ccc ccc cca     288
Val Gly Asp Ile Pro Tyr Asn Asp Phe His Val Arg Gly Pro Pro Pro
                 85                  90                  95 gta tat acc aac ggc aaa aaa ctt gat ggt att tac cag tat ggt cac     336
Val Tyr Thr Asn Gly Lys Lys Leu Asp Gly Ile Tyr Gln Tyr Gly His
```

-continued

```
            100                 105                 110
att gag acc aac gac aac act gct cag ctg ggg ggc aaa tac cga tat       384
Ile Glu Thr Asn Asp Asn Thr Ala Gln Leu Gly Gly Lys Tyr Arg Tyr
            115                 120                 125 ggt gag atc ctt gag tcc gag gga agc atc agg gac ctc cga aac agt       432
Gly Glu Ile Leu Glu Ser Glu Gly Ser Ile Arg Asp Leu Arg Asn Ser
130                 135                 140 ggc tat cgc agt gcc gag aat gca tat gga ggc cac agg ggc ctc ggg       480
Gly Tyr Arg Ser Ala Glu Asn Ala Tyr Gly Gly His Arg Gly Leu Gly
145                 150                 155                 160 cga tac agg gca gca cct gtg ggc agg ctt cac cgg cga gag ctg cag       528
Arg Tyr Arg Ala Ala Pro Val Gly Arg Leu His Arg Arg Glu Leu Gln
                165                 170                 175 cct gga gaa atc cca cct gga gtt gcc act ggg gcg gtg ggc cca ggt       576
Pro Gly Glu Ile Pro Pro Gly Val Ala Thr Gly Ala Val Gly Pro Gly
            180                 185                 190 ggt ttg ctg ggc act gga ggc atg ctg gca gct gat ggc atc ctc gca       624
Gly Leu Leu Gly Thr Gly Gly Met Leu Ala Ala Asp Gly Ile Leu Ala
            195                 200                 205 ggc caa ggt ggc ctg ctc ggc gga ggt ggt ctc ctt ggt gat gga gga       672
Gly Gln Gly Gly Leu Leu Gly Gly Gly Gly Leu Leu Gly Asp Gly Gly
        210                 215                 220 ctt ctt gga gga ggg ggt gtc ctg ggc gtg ctc ggc gag ggt ggc atc       720
Leu Leu Gly Gly Gly Gly Val Leu Gly Val Leu Gly Glu Gly Gly Ile
225                 230                 235                 240 ctc agc act gtg caa ggc atc acg ggg ctg cgt atc gtg gag ctg acc       768
Leu Ser Thr Val Gln Gly Ile Thr Gly Leu Arg Ile Val Glu Leu Thr
                245                 250                 255 ctc cct cgg gtg tcc gtg cgg ctc ctg ccc ggc gtg ggt gtc tac ctg       816
Leu Pro Arg Val Ser Val Arg Leu Leu Pro Gly Val Gly Val Tyr Leu
            260                 265                 270 agc ttg tac acc cgt gtg gcc atc aac ggg aag agt ctt att ggc ttc       864
Ser Leu Tyr Thr Arg Val Ala Ile Asn Gly Lys Ser Leu Ile Gly Phe
            275                 280                 285 ctg gac atc gca gta gaa gtg aac atc aca gcc aag gtc cgg ctg acc       912
Leu Asp Ile Ala Val Glu Val Asn Ile Thr Ala Lys Val Arg Leu Thr
            290                 295                 300 atg gac cgc acg ggt tat cct cgg ctg gtc att gag cga tgt gac acc       960
Met Asp Arg Thr Gly Tyr Pro Arg Leu Val Ile Glu Arg Cys Asp Thr
305                 310                 315                 320 ctc cta ggg ggc atc aaa gtc aag ctg ctg cga ggg ctt ctc ccc aat      1008
Leu Leu Gly Gly Ile Lys Val Lys Leu Leu Arg Gly Leu Leu Pro Asn
                325                 330                 335 ctc gtg gac aat tta gtg aac cga gtc ctg gcc gac gtc ctc cct gac      1056
Leu Val Asp Asn Leu Val Asn Arg Val Leu Ala Asp Val Leu Pro Asp
            340                 345                 350 ttg ctc tgc ccc atc gtg gat gtg gtg ctg ggt ctt gtc aat gac cag      1104
Leu Leu Cys Pro Ile Val Asp Val Val Leu Gly Leu Val Asn Asp Gln
            355                 360                 365 ctg ggc ctc gtg gat tct ctg att cct ctg ggg ata ttg gga agt gtc      1152
Leu Gly Leu Val Asp Ser Leu Ile Pro Leu Gly Ile Leu Gly Ser Val
370                 375                 380 cag tac acc ttc tcc agc ctc ccg ctt gtg acc ggg gaa ttc ctg gag      1200
Gln Tyr Thr Phe Ser Ser Leu Pro Leu Val Thr Gly Glu Phe Leu Glu
385                 390                 395                 400 ctg gac ctc aac acg ctg gtt ggg gag gct gga gga gga ctc atc gac      1248
Leu Asp Leu Asn Thr Leu Val Gly Glu Ala Gly Gly Gly Leu Ile Asp
                405                 410                 415 tac cca ttg ggg tgg cca gct gtg tct ccc aag ccg atg cca gag ctg      1296
```

```
Tyr Pro Leu Gly Trp Pro Ala Val Ser Pro Lys Pro Met Pro Glu Leu
            420                 425                 430 cct ccc atg ggt gac aac acc aag tcc cag ctg gcc atg tct gcc aac     1344
Pro Pro Met Gly Asp Asn Thr Lys Ser Gln Leu Ala Met Ser Ala Asn
            435                 440                 445 ttc ctg ggc tca gtg ctg act cta ctg cag aag cag cat gct cta gac     1392
Phe Leu Gly Ser Val Leu Thr Leu Leu Gln Lys Gln His Ala Leu Asp
450                 455                 460 ctg gat atc acc aat ggc atg ttt gaa gag ctt cct cca ctt acc aca     1440
Leu Asp Ile Thr Asn Gly Met Phe Glu Glu Leu Pro Pro Leu Thr Thr
465                 470                 475                 480 gcc aca ctg gga gcc ctg atc ccc aag gtg ttc cag cag tac ccc gag     1488
Ala Thr Leu Gly Ala Leu Ile Pro Lys Val Phe Gln Gln Tyr Pro Glu
                485                 490                 495 tcc tgc cca ctt atc atc agg atc cag gtg ctg aac cca cca tct gtg     1536
Ser Cys Pro Leu Ile Ile Arg Ile Gln Val Leu Asn Pro Pro Ser Val
            500                 505                 510 atg ctg cag aag gac aaa gcg ctg gtg aag gtg ttg gcc act gcc gag     1584
Met Leu Gln Lys Asp Lys Ala Leu Val Lys Val Leu Ala Thr Ala Glu
            515                 520                 525 gtc atg gtc tcc cag ccc aaa gac ctg gag act acc atc tgc ctc att     1632
Val Met Val Ser Gln Pro Lys Asp Leu Glu Thr Thr Ile Cys Leu Ile
530                 535                 540 gac gtg gac aca gaa ttc ttg gcc tca ttt tcc aca gaa gga gat aag     1680
Asp Val Asp Thr Glu Phe Leu Ala Ser Phe Ser Thr Glu Gly Asp Lys
545                 550                 555                 560 ctc atg att gat gcc aag ctg gag aag acc agc ctc aac ctc aga acc     1728
Leu Met Ile Asp Ala Lys Leu Glu Lys Thr Ser Leu Asn Leu Arg Thr
                565                 570                 575 tca aac gtg ggc aac ttt gat att ggc ctc atg gag gtg ctg gtg gag     1776
Ser Asn Val Gly Asn Phe Asp Ile Gly Leu Met Glu Val Leu Val Glu
            580                 585                 590 aag att ttt gac ctg gca ttc atg ccc gca atg aac gct gtg ctg ggt     1824
Lys Ile Phe Asp Leu Ala Phe Met Pro Ala Met Asn Ala Val Leu Gly
            595                 600                 605 tct ggc gtc cct ctc ccc aaa atc ctc aac atc gac ttt agc aat gca     1872
Ser Gly Val Pro Leu Pro Lys Ile Leu Asn Ile Asp Phe Ser Asn Ala
            610                 615                 620 gac att gac gtg ttg gag gac ctt ttg gtg ctg agc gca tga             1914
Asp Ile Asp Val Leu Glu Asp Leu Leu Val Leu Ser Ala
625                 630                 635

<210> SEQ ID NO 4
<211> LENGTH: 637
<212> TYPE: PRT
<213> ORGANISM: Homo sapiens

<400> SEQUENCE: 4

Met Trp Met Ala Trp Cys Val Ala Ala Leu Ser Val Val Ala Val Cys
1               5                   10                  15

Gly Thr Ser His Glu Thr Asn Thr Val Leu Arg Val Thr Lys Asp Val
            20                  25                  30

Leu Ser Asn Ala Ile Ser Gly Met Leu Gln Gln Ser Asp Ala Leu His
        35                  40                  45

Ser Ala Leu Arg Glu Val Pro Leu Gly Lys Ala Arg Gly Asp Gly Gly
    50                  55                  60

Gly Pro Leu Leu Gly Gly Leu Leu Gly Gly Ser Gly Ser Gly Gly Gly
65                  70                  75                  80

Val Gly Asp Ile Pro Tyr Asn Asp Phe His Val Arg Gly Pro Pro Pro
```

-continued

```
                85                  90                  95
Val Tyr Thr Asn Gly Lys Lys Leu Asp Gly Ile Tyr Gln Tyr Gly His
            100                 105                 110
Ile Glu Thr Asn Asp Asn Thr Ala Gln Leu Gly Gly Lys Tyr Arg Tyr
            115                 120                 125
Gly Glu Ile Leu Glu Ser Gly Ser Ile Arg Asp Leu Arg Asn Ser
    130                 135                 140
Gly Tyr Arg Ser Ala Glu Asn Ala Tyr Gly Gly His Arg Gly Leu Gly
145                 150                 155                 160
Arg Tyr Arg Ala Ala Pro Val Gly Arg Leu His Arg Arg Glu Leu Gln
                165                 170                 175
Pro Gly Glu Ile Pro Pro Gly Val Ala Thr Gly Ala Val Gly Pro Gly
            180                 185                 190
Gly Leu Leu Gly Thr Gly Gly Met Leu Ala Ala Asp Gly Ile Leu Ala
            195                 200                 205
Gly Gln Gly Gly Leu Leu Gly Gly Gly Leu Gly Asp Gly Gly
    210                 215                 220
Leu Leu Gly Gly Gly Val Leu Gly Val Leu Gly Glu Gly Gly Ile
225                 230                 235                 240
Leu Ser Thr Val Gln Gly Ile Thr Gly Leu Arg Ile Val Glu Leu Thr
                245                 250                 255
Leu Pro Arg Val Ser Val Arg Leu Leu Pro Gly Val Gly Val Tyr Leu
            260                 265                 270
Ser Leu Tyr Thr Arg Val Ala Ile Asn Gly Lys Ser Leu Ile Gly Phe
            275                 280                 285
Leu Asp Ile Ala Val Glu Val Asn Ile Thr Ala Lys Val Arg Leu Thr
            290                 295                 300
Met Asp Arg Thr Gly Tyr Pro Arg Leu Val Ile Glu Arg Cys Asp Thr
305                 310                 315                 320
Leu Leu Gly Gly Ile Lys Val Lys Leu Leu Arg Gly Leu Leu Pro Asn
                325                 330                 335
Leu Val Asp Asn Leu Val Asn Arg Val Leu Ala Asp Val Leu Pro Asp
            340                 345                 350
Leu Leu Cys Pro Ile Val Asp Val Leu Gly Leu Val Asn Asp Gln
            355                 360                 365
Leu Gly Leu Val Asp Ser Leu Ile Pro Leu Gly Ile Leu Gly Ser Val
    370                 375                 380
Gln Tyr Thr Phe Ser Ser Leu Pro Leu Val Thr Gly Glu Phe Leu Glu
385                 390                 395                 400
Leu Asp Leu Asn Thr Leu Val Gly Glu Ala Gly Gly Gly Leu Ile Asp
            405                 410                 415
Tyr Pro Leu Gly Trp Pro Ala Val Ser Pro Lys Pro Met Pro Glu Leu
            420                 425                 430
Pro Pro Met Gly Asp Asn Thr Lys Ser Gln Leu Ala Met Ser Ala Asn
            435                 440                 445
Phe Leu Gly Ser Val Leu Thr Leu Leu Gln Lys Gln His Ala Leu Asp
    450                 455                 460
Leu Asp Ile Thr Asn Gly Met Phe Glu Glu Leu Pro Pro Leu Thr Thr
465                 470                 475                 480
Ala Thr Leu Gly Ala Leu Ile Pro Lys Val Phe Gln Gln Tyr Pro Glu
            485                 490                 495
Ser Cys Pro Leu Ile Ile Arg Ile Gln Val Leu Asn Pro Pro Ser Val
            500                 505                 510
```

```
Met Leu Gln Lys Asp Lys Ala Leu Val Lys Val Leu Ala Thr Ala Glu
        515                 520                 525

Val Met Val Ser Gln Pro Lys Asp Leu Glu Thr Thr Ile Cys Leu Ile
    530                 535                 540

Asp Val Asp Thr Glu Phe Leu Ala Ser Phe Ser Thr Glu Gly Asp Lys
545                 550                 555                 560

Leu Met Ile Asp Ala Lys Leu Glu Lys Thr Ser Leu Asn Leu Arg Thr
            565                 570                 575

Ser Asn Val Gly Asn Phe Asp Ile Gly Leu Met Glu Val Leu Val Glu
        580                 585                 590

Lys Ile Phe Asp Leu Ala Phe Met Pro Ala Met Asn Ala Val Leu Gly
        595                 600                 605

Ser Gly Val Pro Leu Pro Lys Ile Leu Asn Ile Asp Phe Ser Asn Ala
    610                 615                 620

Asp Ile Asp Val Leu Glu Asp Leu Leu Val Leu Ser Ala
625                 630                 635
```

LIPID BINDING PROTEIN 4

FIELD OF THE INVENTION

This invention relates to newly identified polypeptides and polynucleotides encoding such polypeptides sometimes hereinafter referred to as "New Lipid Binding Protein 4 (NLIBP4)", to their use in diagnosis and in identifying compounds that may be agonists, antagonists that are potentially useful in therapy, and to production of such polypeptides and polynucleotides.

BACKGROUND OF THE INVENTION

The drug discovery process is currently undergoing a fundamental revolution as it embraces "functional genomics", that is, high throughput genome- or gene-based biology. This approach as a means to identify genes and gene products as therapeutic targets is rapidly superceding earlier approaches based on "positional cloning". A phenotype, that is a biological function or genetic disease, would be identified and this would then be tracked back to the responsible gene, based on its genetic map position.

Functional genomics relies heavily on high-throughput DNA sequencing technologies and the various tools of bioinformatics to identify gene sequences of potential interest from the many molecular biology databases now available. There is a continuing need to identify and characterise further genes and their related polypeptides/proteins, as targets for drug discovery.

SUMMARY OF THE INVENTION

The present invention relates to New Lipid Binding Protein 4, in particular New Lipid Binding Protein 4 polypeptides and New Lipid Binding Protein 4 polynucleotides, recombinant materials and methods for their production. Such polypeptides and polynucleotides are of interest in relation to methods of treatment of certain diseases, including, but not limited to, cancer, bacteremia, endotoximia, meningococcemia, hemorrhagic trauma, partial hepatectomy, severe peritoneal infections, cystic fibrosis, coronary heart disease, artheriosclerosis hereinafter referred to as "diseases of the invention". In a further aspect, the invention relates to methods for identifying agonists and antagonists (e.g., inhibitors) using the materials provided by the invention, and treating conditions associated with New Lipid Binding Protein 4 imbalance with the identified compounds. In a still further aspect, the invention relates to diagnostic assays for detecting diseases associated with inappropriate New Lipid Binding Protein 4 activity or levels.

DESCRIPTION OF THE INVENTION

In a first aspect, the present invention relates to New Lipid Binding Protein 4 polypeptides. Such polypeptides include:

(a) a polypeptide encoded by a polynucleotide comprising the sequence of SEQ ID NO:1;

(b) a polypeptide comprising a polypeptide sequence having at least 95%, 96%, 97%, 98%, or 99% identity to the polypeptide sequence of SEQ ID NO:2;

(c) a polypeptide comprising the polypeptide sequence of SEQ ID NO:2;

(d) a polypeptide having at least 95%, 96%, 97%, 98%, or 99% identity to the polypeptide sequence of SEQ ID NO:2;

(e) the polypeptide sequence of SEQ ID NO:2; and (f) a polypeptide having or comprising a polypeptide sequence that has an Identity Index of 0.95, 0.96, 0.97, 0.98, or 0.99 compared to the polypeptide sequence of SEQ ID NO:2;

(g) fragments and variants of such polypeptides in (a) to (f).

Polypeptides of the present invention are believed to be members of the Lipid Binding Proteins, such as lipopolysaccharide-binding protein (LBP) or bactericidial/permeability-increasing protein (BPI). They are therefore of interest because lipid binding proteins show high-affinity binding to lipopolysaccharide (LPS), a glycolipid found in the outer membrane of gram negative bacteria. Accordingly, lipid binding proteins play a decisive role in the host defense against bacterial infections.

Further, all of the known members of the protein family of lipid binding proteins are able to bind phospholipids. LBP, cholesteryl ester transfer protein (CETP) and phospholipid-transfer protein (PLTP) can also bind cholesterol and high-density lipoproteins (HDL). HDL plasma levels are inversely correlated with coronary heart disease and artherosclerosis. Lipid binding and transfer proteins, such as CETP and PLTP, facilitate the transfer of phospholipids and cholesterol from triglyceride-rich lipoproteins (TRL) into HDL. Accordingly, members of the family of lipid binding proteins are thought to play a role in the prevention of these disease.

Further, LBP is an acute phase serum protein secreted by the liver that catalyses the transfer of LPS monomers to CD14 thereby facilitating a broad spectrum of cellular and tissue responses leading to antibacterial and proinflammatory activities. BPI is a 456-residue cationic protein produced by polymorphonuclear leukocytes (PMN) and is stored in the primary granules of these cells. The biological effects of isolated BPI are linked to complex formation with LPS. Binding of BPI to live bacteria via LPS causes immediate growth arrest. Complex formation of BPI with cell-associated or cell-free LPS inhibits all LPS-induced host cell responses. BPI-blocking antibodies abolish the potent activity of whole PMN lysates and inflammatory fluids against BPI-sensitive bacteria. The antibacterial and the antiendotoxin activities of BPI are fully expressed by the amino terminal half of the molecule. These properties of BPI have prompted preclinical and subsequent clinical testing of recombinant amino-terminal fragments of BPI. In animals, human BPI protein products protect against lethal injections of isolated LPS. Phase I trials in healthy human volunteers and multiple Phase I/II clinical trials have been completed or are in progress (severe pediatric meningococcemia, hemorrhagic trauma, partial hepatectomy, severe peritoneal infections, and cystic fibrosis) and phase III trials (meningococcemia and hemorrhagic trauma) have been initiated. In none of >900 normal and severely ill individuals have issues of safety or immunogenicity been encountered. Preliminary evidence points to overall benefit in BPI-treated patients. These results suggest that BPI, but also other lipid binding protein such as the present invention, may have a place in the treatment of life-threatening infections and conditions associated with bacteremia and endotoxemia.

The amino acid sequence of NLIBP4 shows significant homology to other members of the protein family of lipid binding proteins such as LBP, BPI and CETP. NLIBP4 contains several amino acids which are conserved betwen the other members of the protein family of lipid binding proteins such as Prolin-266, Cystein-318, Cystein-355, Prolin-392, which corresponds e.g. to the amino acids Prolin-97, Cystein-159, Cystein-198, Prolin-236 in LBP, respectively. Further, NLiBP4 shows a similar exon/intron organisation to LBP, BPI, NLIBP1, NLiBP2, NLiBP3, and CETP, suggesting that (i) NLIBP4 like other members of the protein family of lipid binding proteins, has evolved from a common primordial gene and (ii) that these proteins share similar functional properties.

A further aspect relates to the finding that NLIBP1 is downregulated in tumor tissues, e.g. in larynx carcinomas. This finding indicates a role of lipid binding proteins such as New Lipid Binding Protein 4 in mechanisms of immune escape of the tumor and as such gives a rationale for therapeutic interventions.

The biological properties of the New Lipid Binding Protein, 4 are hereinafter referred to as "biological activity of New Lipid Binding Protein 4" or "New Lipid Binding Protein 4 activity". Preferably, a polypeptide of the present invention exhibits at least one biological activity of New Lipid Binding Protein 4.

Polypeptides of the present invention also includes variants of the aforementioned polypeptides, including all allelic forms and splice variants. Such polypeptides vary from the reference polypeptide by insertions, deletions, and substitutions that may be conservative or non-conservative, or any combination thereof. Particularly preferred variants are those in which several, for instance from 50 to 30, from 30 to 20, from 20 to 10, from 10 to 5, from 5 to 3, from 3 to 2, from 2 to 1 or 1 amino acids are inserted, substituted, or deleted, in any combination.

Preferred fragments of polypeptides of the present invention include a polypeptide comprising an amino acid sequence having at least 30, 50 or 100 contiguous amino acids from the amino acid sequence of SEQ ID NO: 2 or SEQ ID NO: 4, or a polypeptide comprising an amino acid sequence having at least 30, 50 or 100 contiguous amino acids truncated or deleted from the amino acid sequence of SEQ ID NO: 2 or SEQ ID NO: 4. Preferred fragments are biologically active fragments that mediate the biological activity of New Lipid Binding Protein 4, including those with a similar activity or an improved activity, or with a decreased undesirable activity. Also preferred are those fragments that are antigenic or immunogenic in an animal, especially in a human.

Fragments of the polypeptides of the invention may be employed for producing the corresponding full-length polypeptide by peptide synthesis; therefore, these variants may be employed as intermediates for producing the full-length polypeptides of the invention. The polypeptides of the present invention may be in the form of the "mature" protein or may be a part of a larger protein such as a precursor or a fusion protein. It is often advantageous to include an additional amino acid sequence that contains secretory or leader sequences, pro-sequences, sequences that aid in purification, for instance multiple histidine residues, or an additional sequence for stability during recombinant production.

Polypeptides of the present invention can be prepared in any suitable manner, for instance by isolation form naturally occuring sources, from genetically engineered host cells comprising expression systems (vide infra) or by chemical synthesis, using for instance automated peptide synthesisers, or a combination of such methods. Means for preparing such polypeptides are well understood in the art.

In a further aspect, the present invention relates to New Lipid Binding Protein 4 polynucleotides. Such polynucleotides include:

(a) a polynucleotide comprising a polynucleotide sequence having at least 95%, 96%, 97%, 98%, or 99% identity to the polynucleotide squence of SEQ ID NO: 1 or SEQ ID NO: 3;

(b) a polynucleotide comprising the polynucleotide of SEQ ID NO:1 or SEQ ID NO: 3;

(c) a polynucleotide having at least 95%, 96%, 97%, 98%, or 99% identity to the polynucteotide of SEQ ID NO:1 or SEQ ID NO: 3;

(d) the polynucleotide of SEQ ID NO:1 or SEQ ID NO: 3;

(e) a polynucleotide comprising a polynucleotide sequence encoding a polypeptide sequence having at least 95%, 96%, 97%, 98%, or 99% identity to the polypeptide sequence of SEQ ID NO:2 or SEQ ID NO: 4;

(f) a polynucleotide comprising a polynucleotide sequence encoding the polypeptide of SEQ ID NO:2 or SEQ ID NO: 4;

(g) a polynucleotide having a polynucleotide sequence encoding a polypeptide sequence having at least 95%, 96%, 97%, 98%, or 99% identity to the polypeptide sequence of SEQ ID NO:2 or SEQ ID NO: 4;

(h) a polynucleotide encoding the polypeptide of SEQ ID NO:2 or SEQ ID NO: 4;

(i) a polynucleotide having or comprising a polynucleotide sequence that has an Identity Index of 0.95, 0.96, 0.97, 0.98, or 0.99 compared to the polynucleotide sequence of SEQ ID NO:1 or SEQ ID NO: 3.

(j) a polynucleotide having or comprising a polynucleotide sequence encoding a polypeptide sequence that has an Identity Index of 0.95, 0.96, 0.97, 0.98, or 0.99 compared to the polypeptide sequence of SEQ ID NO:2 or SEQ ID NO: 4; and polynucleotides that are fragments and variants of the above mentioned polynucleotides or that are complementary to above mentioned polynucleotides, over the entire length thereof.

Preferred fragments of polynucleotides of the present invention include a polynucleotide comprising an nucleotide sequence having at least 15, 30, 50 or 100 contiguous nucleotides from the sequence of SEQ ID NO: 1 or SEQ ID NO: 3, or a polynucleotide comprising an sequence having at least 30, 50 or 100 contiguous nucleotides truncated or deleted from the sequence of SEQ ID NO: 1 or SEQ ID NO: 3.

Preferred variants of polynucleotides of the present invention include splice variants, allelic variants, and polymorphisms, including polynucleotides having one or more single nucleotide polymorphisms (SNPs).

Polynucleotides of the present invention also include polynucleotides encoding polypeptide variants that comprise the amino acid sequence of SEQ ID NO: 2 or SEQ ID NO: 4 and in which several, for instance from 50 to 30, from 30 to 20, from 20 to 10, from 10 to 5, from 5 to 3, from 3 to 2, from 2 to 1 or 1 amino acid residues are substituted, deleted or added, in any combination.

In a further aspect, the present invention provides polynucleotides that are RNA transcripts of the DNA sequences of the present invention. Accordingly, there is provided an RNA polynucleotide that:

(a) comprises an RNA transcript of the DNA sequence encoding the polypeptide of SEQ ID NO: 2 or SEQ ID NO: 4;

(b) is the RNA transcript of the DNA sequence encoding the polypeptide of SEQ ID NO:2 or SEQ ID NO: 4;

(c) comprises an RNA transcript of the DNA sequence of SEQ ID NO:1 or SEQ ID NO: 3; or (d) is the RNA transcript of the DNA sequence of SEQ ID NO:1 or SEQ ID NO: 3;

and RNA polynucleotides that are complementary thereto.

The polynucleotide sequence of SEQ ID NO:1 or SEQ ID NO: 3 shows homology with bactericidal/permeability-increasing protein (Acc.: NM_001725); lipopolysaccharide-binding protein (Acc.: AF105067); cholesteryl ester transfer protein (Acc.:NM_000078); phospholipid transfer protein (Acc.: NM_006227). The polynucleotide sequence of SEQ ID NO:1 or SEQ ID NO: 3 is a cDNA sequence that encodes the polypeptide of SEQ ID NO:2 or SEQ ID NO: 4. The polynucleotide sequence encoding the polypeptide of SEQ ID NO:2 or SEQ ID NO: 4 may be identical to the polypeptide encoding sequence of SEQ ID NO:1 or SEQ ID NO: 3 or it may be a sequence other than SEQ ID NO:1 or SEQ ID NO: 3, which, as a result of the redundancy (degeneracy) of the genetic code, also encodes the polypeptide of SEQ ID NO:2 or SEQ ID NO: 4. The polypeptide of the SEQ ID NO:2 or SEQ ID NO: 4 is related to other proteins of the Lipid Binding Proteins family, having homology and/or structural similarity with bactericidal/permeability-increasing protein (Acc.: NP_001716); lipopolysaccharide-binding protein (Acc.:P18428); cholesteryl ester transfer protein (Acc.: NP_000069); phospholipid transfer protein (Acc.: NP_006218).

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one New Lipid Binding Protein 4 activity.

Polynucleotides of the present invention may be obtained using standard cloning and screening techniques from a cDNA library derived from mRNA in cells of human trachea, larynx, larynx carcinoma, palate, pharynx, endometrium, olfactory epithelium, (see for instance, Sambrook et al., Molecular Cloning: A Laboratory Manual, 2nd Ed., Cold Spring Harbor Laboratory Press, Cold Spring Harbor, N.Y. (1989)). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself, or the coding sequence for the mature polypeptide in reading frame with other coding sequences, such as those encoding a leader or secretory sequence, a pre-, or pro- or prepro-protein sequence, or other fusion peptide portions. For example, a marker sequence that facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Polynucleotides that are identical, or have sufficient identity to a polynucleotide sequence of SEQ ID NO:1 or SEQ ID NO: 3, may be used as hybridization probes for cDNA and genomic DNA or as primers for a nucleic acid amplification reaction (for instance, PCR). Such probes and primers may be used to isolate full-length cDNAs and genomic clones encoding polypeptides of the present invention and to isolate cDNA and genomic clones of other genes (including genes encoding paralogs from human sources and orthologs and paralogs from species other than human) that have a high sequence similarity to SEQ ID NO:1 or SEQ ID NO: 3, typically at least 95% identity. Preferred probes and primers will generally comprise at least 15 nucleotides, preferably, at least 30 nucleotides and may have at least 50, if not at least 100 nucleotides. Particularly preferred probes will have between 30 and 50 nucleotides. Particularly preferred primers will have between 20 and 25 nucleotides.

A polynucleotide encoding a polypeptide of the present invention, including homologs from species other than human, may be obtained by a process comprising the steps of screening a library under stringent hybridization conditions with a labeled probe having the sequence of SEQ ID NO: 1 or SEQ ID NO: 3 or a fragment thereof, preferably of at least 15 nucleotides; and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 microgram/ml denatured, sheared salmon sperm DNA; followed by washing the filters in 0.1×SSC at about 65° C. Thus the present invention also includes isolated polynucleotides, preferably with a nucleotide sequence of at least 100, obtained by screening a library under stringent hybridization conditions with a labeled probe having the sequence of SEQ ID NO:1 or SEQ ID NO: 3 or a fragment thereof, preferably of at least 15 nucleotides.

The skilled artisan will appreciate that, in many cases, an isolated cDNA sequence will be incomplete, in that the region coding for the polypeptide does not extend all the way through to the 5' terminus. This is a consequence of reverse transcriptase, an enzyme with inherently low "processivity" (a measure of the ability of the enzyme to remain attached to the template during the polymerisation reaction), failing to complete a DNA copy of the mRNA template during first strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., Proc Nat Acad Sci USA 85, 8998–9002, 1988). Recent modifications of the technique, exemplified by the Marathon (trade mark) technology (Clontech Laboratories Inc.) for example, have significantly simplified the search for longer cDNAs. In the Marathon (trade mark) technology, cDNAs have been prepared from mRNA extracted from a chosen tissue and an 'adaptor' sequence ligated onto each end. Nucleic acid amplification (PCR) is then carried out to amplify the "missing" 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analysed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems comprising a polynucleotide or polynucleotides of the present invention, to host cells which are genetically engineered with such expression sytems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Polynucleotides may be introduced into host cells by methods described in many standard laboratory manuals, such as Davis et al., Basic Methods in Molecular Biology (1986) and Sambrook et al. (ibid). Preferred methods of introducing polynucleotides into host cells include, for instance, calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as *Streptococci, Staphylococci, E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector that is able to maintain, propagate or express a polynucleotide to produce a polypeptide in a host may be used. The appropriate polynucleotide sequence may be inserted into an expression system by any of a variety of well-known and routine techniques, such as, for example, those set forth in Sambrook et al., (ibid). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during intracellular synthesis, isolation and/or purification.

Polynucleotides of the present invention may be used as diagnostic reagents, through detecting mutations in the associated gene. Detection of a mutated form of the gene characterised by the polynucleotide of SEQ ID NO: 1 or SEQ ID NO: 3 in the cDNA or genomic sequence and which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques well known in the art.

Nucleic acids for diagnosis may be obtained from a subject's cells, such as from blood, urine, saliva, tissue biopsy or autopsy material. The genomic DNA may be used directly for detection or it may be amplified enzymatically by using PCR, preferably RT-PCR, or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled New Lipid Binding Protein 4 nucleotide sequences. Perfectly matched sequences can be distinguished from mismatched duplexes by RNase digestion or by differences in melting temperatures. DNA sequence difference may also be detected by alterations in the electrophoretic mobility of DNA fragments in gels, with or without denaturing agents, or by direct DNA sequencing (see, for instance, Myers et al., Science (1985) 230:1242). Sequence changes at specific locations may also be revealed by nuclease protection assays, such as RNase and S1 protection or the chemical cleavage method (see Cotton et al., Proc Natl Acad Sci USA (1985) 85: 4397–4401).

An array of oligonucleotides probes comprising New Lipid Binding Protein 4 polynucleotide sequence or fragments thereof can be constructed to conduct efficient screening of e.g., genetic mutations. Such arrays are preferably high density arrays or grids. Array technology methods are well known and have general applicability and can be used to address a variety of questions in molecular genetics including gene expression, genetic linkage, and genetic variability, see, for example, M. Chee et al., Science, 274, 610–613 (1996) and other references cited therein.

Detection of abnormally decreased or increased levels of polypeptide or mRNA expression may also be used for diagnosing or determining susceptibility of a subject to a disease of the invention. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radioimmunoassays, competitive-binding assays, Western Blot analysis and ELISA assays.

Thus in another aspect, the present invention relates to a diagonostic kit comprising:

(a) a polynucleotide of the present invention, preferably the nucleotide sequence of SEQ ID NO: 1 or SEQ ID NO: 3, or a fragment or an RNA transcript thereof;

(b) a nucleotide sequence complementary to that of (a);

(c) a polypeptide of the present invention, preferably the polypeptide of SEQ ID NO:2 or SEQ ID NO: 4 or a fragment thereof; or (d) an antibody to a polypeptide of the present invention, preferably to the polypeptide of SEQ ID NO:2 or SEQ ID NO: 4.

It will be appreciated that in any such kit, (a), (b), (c) or (d) may comprise a substantial component. Such a kit will be of use in diagnosing a disease or susceptibility to a disease, particularly diseases of the invention, amongst others.

The polynucleotide sequences of the present invention are valuable for chromosome localisation studies. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (co-inheritance of physically adjacent genes). Precise human chromosomal localisations for a genomic sequence (gene fragment etc.) can be determined using Radiation Hybrid (RH) Mapping (Walter, M. Spillett, D., Thomas, P., Weissenbach; J., and Goodfellow, P., (1994) A method for constructing radiation hybrid maps of whole genomes, Nature Genetics 7, 22–28). A number of RH panels are available from Research Genetics (Huntsville, Ala., USA) e.g. the GeneBridge4 RH panel (Hum Mol Genet March 1996; 5(3):339–46 A radiation hybrid map of the human genome. Gyapay G, Schmitt K, Fizames C, Jones H, Vega-Czarny N, Spillett D, Muselet D, Prud'Homme J F, Dib. C, Auffray C, Morissette J, Weissenbach J, Goodfellow P N). To determine the chromosomal location of a gene using this panel, 93 PCRs are performed using primers designed from the gene of interest on RH DNAs. Each of these DNAs contains random human genomic fragments maintained in a hamster background (human/hamster hybrid cell lines). These PCRs result in 93 scores indicating the presence or absence of the PCR product of the gene of interest. These scores are compared with scores created using PCR products from genomic sequences of known location. This comparison is conducted at http://www.genome.wi.mit.edu/. The gene of the present invention maps to human chromosome 20.

The polynucleotide sequences of the present invention are also valuable tools for tissue expression studies. Such studies allow the determination of expression patterns of polynucleotides of the present invention which may give an indication as to the expression patterns of the encoded polypeptides in tissues, by detecting the mRNAs that encode them. The techniques used are well known in the art and include in situ hydridisation techniques to clones arrayed on a grid, such as cDNA microarray hybridisation (Schena et al, Science, 270, 467–470, 1995 and Shalon et al, Genome Res, 6, 639–645, 1996) and nucleotide amplification techniques such as PCR. A preferred method uses the TAQMAN (Trade mark) technology available from Perkin Elmer. Results from these studies can provide an indication of the normal function of the polypeptide in the organism. In addition, comparative studies of the normal expression pattern of mRNAs with that of mRNAs encoded by an alternative form of the same gene (for example, one having an alteration in polypeptide coding potential or a regulatory mutation) can provide valuable insights into the role of the polypeptides of the present invention, or that of inappropriate expression thereof in disease. Such inappropriate expression may be of a temporal, spatial or simply quantitative nature.

The polypeptides of the present invention are expressed in trachea, larynx, larynx carcinoma, palate, pharynx, endometrium, olfactory epithelium.

A further aspect of the present invention relates to antibodies. The polypeptides of the invention or their fragments, or cells expressing them, can be used as immunogens to produce antibodies that are immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Immunology Today (1983) 4:72) and the EBV-hybridoma technique (Cole et al., Monoclonal Antibodies and Cancer Therapy, 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography. Antibodies against polypeptides of the present invention may also be employed to treat diseases of the invention, amongst others.

Polypeptides and polynucleotides of the present invention may also be used as vaccines. Accordingly, in a further aspect, the present invention relates to a method for inducing an immunological response in a mammal that comprises inoculating the mammal with a polypeptide of the present invention, adequate to produce antibody and/or T cell immune response, including, for example, cytokine-producing T cells or cytotoxic T cells, to protect said animal from disease, whether that disease is already established within the individual or not. An immunological response in a mammal may also be induced by a method comprises delivering a polypeptide of the present invention via a vector directing expression of the polynucleotide and coding for the polypeptide in vivo in order to induce such an immunological response to produce antibody to protect said animal from diseases of the invention. One way of administering the vector is by accelerating it into the desired cells as a coating on particles or otherwise. Such nucleic acid vector may comprise DNA, RNA, a modified nucleic acid, or a DNA/RNA hybrid. For use a vaccine, a polypeptide or a nucleic acid vector will be normally provided as a vaccine formulation (composition). The formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions that may contain anti-oxidants, buffers, bacteriostats and solutes that render the formulation instonic with the blood of the recipient; and aqueous and non-aqueous sterile suspensions that may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Polypeptides of the present invention have one or more biological functions that are of relevance in one or more disease states, in particular the diseases of the invention hereinbefore mentioned. It is therefore useful to to identify compounds that stimulate or inhibit the function or level of the polypeptide. Accordingly, in a further aspect, the present invention provides for a method of screening compounds to identify those that stimulate or inhibit the function or level of the polypeptide. Such methods identify agonists or antagonists that may be employed for therapeutic and prophylactic purposes for such diseases of the invention as hereinbefore mentioned. Compounds may be identified from a variety of sources, for example, cells, cell-free preparations, chemical libraries, collections of chemical compounds, and natural product mixtures. Such agonists or antagonists so-identified may be natural or modified substrates, ligands, receptors, enzymes, etc., as the case may be, of the polypeptide; a structural or functional mimetic thereof (see Coligan et al., Current Protocols in Immunology 1(2):Chapter 5 (1991)) or a small molecule.

The screening method may simply measure the binding of a candidate compound to the polypeptide, or to cells or membranes bearing the polypeptide, or a fusion protein thereof, by means of a label directly or indirectly associated with the candidate compound. Alternatively, the screening method may involve measuring or detecting (qualitatively or quantitatively) the competitive binding of a candidate compound to the polypeptide against a labeled competitor (e.g. agonist or antagonist). Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Further, the screening methods may simply comprise the steps of mixing a candidate compound with a solution containing a polypeptide of the present invention, to form a mixture, measuring a New Lipid Binding Protein 4 activity in the mixture, and comparing the New Lipid Binding Protein 4 activity of the mixture to a control mixture which contains no candidate compound.

Polypeptides of the present invention may be employed in conventional low capacity screening methods and also in high-throughput screening (HTS) formats. Such HTS formats include not only the well-established use of 96- and, more recently, 384-well micotiter plates but also emerging methods such as the nanowell method described by Schullek et al, Anal Biochem., 246, 20–29, (1997).

Fusion proteins, such as those made from Fc portion and New Lipid Binding Protein 4 polypeptide, as hereinbefore described, can also be used for high-throughput screening assays to identify antagonists for the polypeptide of the present invention (see D. Bennett et al., J Mol Recognition, 8:52–58 (1995); and K. Johanson et al., J Biol Chem, 270(16):9459–9471 (1995)).

Screening Techniques

The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents that may inhibit or enhance the production of polypeptide (also called antagonist or agonist, respectively) from suitably manipulated cells or tissues.

A polypeptide of the present invention may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the receptor (cells, cell membranes, cell supernatants, tissue extracts, bodily fluids). Other methods include biophysical techniques such as surface plasmon resonance and spectroscopy. These screening methods may also be used to identify agonists and antagonists of the polypeptide that compete with the binding of the polypeptide to its receptors, if any. Standard methods for conducting such assays are well understood in the art.

Examples of antagonists of polypeptides of the present invention include antibodies or, in some cases, oligonucleotides or proteins that are closely related to the ligands, substrates, receptors, enzymes, etc., as the case may be, of the polypeptide, e.g., a fragment of the ligands, substrates, receptors, enzymes, etc.; or a small molecule that bind to the polypeptide of the present invention but do not elicit a response, so that the activity of the polypeptide is prevented.

Screening methods may also involve the use of transgenic technology and New Lipid Binding Protein 4 gene. The art of constructing transgenic animals is well established. For example, the New Lipid Binding Protein 4 gene may be introduced through microinjection into the male pronucleus of fertilized oocytes, retroviral transfer into pre- or post-implantation embryos, or injection of genetically modified, such as by electroporation, embryonic stem cells into host blastocysts. Particularly useful transgenic animals are so-called "knock-in" animals in which an animal gene is replaced by the human equivalent within the genome of that animal. Knock-in transgenic animals are useful in the drug discovery process, for target validation, where the compound is specific for the human target. Other useful transgenic animals are so-called "knock-out" animals in which the expression of the animal ortholog of a polypeptide of the present invention and encoded by an endogenous DNA sequence in a cell is partially or completely annulled. The gene knock-out may be targeted to specific cells or tissues, may occur only in certain cells or tissues as a consequence of the limitations of the technology, or may occur in all, or substantially all, cells in the animal. Transgenic animal technology also offers a whole animal expression-cloning system in which introduced genes are expressed to give large amounts of polypeptides of the present invention.

Screening kits for use in the above described methods form a further aspect of the present invention. Such screening kits comprise:

(a) a polypeptide of the present invention;

(b) a recombinant cell expressing a polypeptide of the present invention;

(c) a cell membrane expressing a polypeptide of the present invention; or (d) an antibody to a polypeptide of the present invention;

which polypeptide is preferably that of SEQ ID NO:2 or SEQ ID NO: 4.

It will be appreciated that in any such kit, (a), (b), (c) or (d) may comprise a substantial component.

Glossary

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide" generally refers to any polyribonucleotide (RNA) or polydeoxribonucleotide (DNA), which may be unmodified or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any polypeptide comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques that are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, Proteins—Structure and Molecular Properties, 2nd Ed., T. E. Creighton, W. H. Freeman and Company, New York, 1993; Wold, F., Post-translational Protein Modifications: Perspectives and Prospects, 1–12, in Post-translational Covalent Modification of Proteins, B. C. Johnson, Ed., Academic Press, New York, 1983; Seifter et al., "Analysis for protein modifications and nonprotein cofactors", Meth Enzymol, 182, 626–646, 1990, and Rattan et al., "Protein Synthesis: Post-translational Modifications and Aging", Ann NY Acad Sci, 663, 48–62, 1992).

"Fragment" of a polypeptide sequence refers to a polypeptide sequence that is shorter than the reference sequence but that retains essentially the same biological function or activity as the reference polypeptide. "Fragment" of a polynucleotide sequence refers to a polynucleotide sequence that is shorter than the reference sequence of SEQ ID NO:1 or SEQ ID NO: 3.

"Variant" refers to a polynucleotide or polypeptide that differs from a reference polynucleotide or polypeptide, but retains the essential properties thereof. A typical variant of a polynucleotide differs in nucleotide sequence from the reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from the reference polypeptide. Generally, alterations are limited so that the sequences of the reference polypeptide and the variant are closely similar overall and, in many regions, identical. A variant and reference polypeptide may differ in amino acid sequence by one or more substitutions, insertions, deletions in any combination. A substituted or inserted amino acid residue may or may not be one encoded by the genetic code. Typical conservative substitutions include Gly, Ala; Val, Ile, Leu; Asp, Glu; Asn, Gln; Ser, Thr; Lys, Arg; and Phe and Tyr. A variant of a polynucleotide or polypeptide may be naturally occurring such as an allele, or it may be a variant that is, not known to occur naturally. Non-naturally occurring variants of polynucleotides and polypeptides may be made by mutagenesis techniques or by direct synthesis. Also included as variants are polypeptides having one or more post-translational modifications, for instance glycosylation, phosphorylation, methylation, ADP ribosylation and the like. Embodiments include methylation of the N-terminal amino acid, phosphorylations of serines and threonines and modification of C-terminal glycines.

"Allele" refers to one of two or more alternative forms of a gene occuring at a given locus in the genome.

"Polymorphism" refers to a variation in nucleotide sequence (and encoded polypeptide sequence, if relevant) at a given position in the genome within a population.

"Single Nucleotide Polymorphism" (SNP) refers to the occurence of nucleotide variability at a single nucleotide position in the genome, within a population. An SNP may occur within a gene or within intergenic regions of the genome. SNPs can be assayed using Allele Specific Amplification (ASA). For the process at least 3 primers are required. A common primer is used in reverse complement to the polymorphism being assayed. This common primer can be between 50 and 1500 bps from the polymorphic base. The other two (or more) primers are identical to each other except that the final 3' base wobbles to match one of the two (or more) alleles that make up the polymorphism. Two (or more) PCR reactions are then conducted on sample DNA, each using the common primer and one of the Allele Specific Primers.

"Splice Variant" as used herein refers to cDNA molecules produced from RNA molecules initially transcribed from the same genomic DNA sequence but which have undergone alternative RNA splicing. Alternative RNA splicing occurs when a primary RNA transcript undergoes splicing, generally for the removal of introns, which results in the production of more than one mRNA molecule each of that may encode different amino acid sequences. The term splice variant also refers to the proteins encoded by the above cDNA molecules.

"Identity" reflects a relationship between two or more polypeptide sequences or two or more polynucleotide sequences, determined by comparing the sequences. In general, identity refers to an exact nucleotide to nucleotide or amino acid to amino acid correspondence of the two polynucleotide or two polypeptide sequences, respectively, over the length of the sequences being compared.

"% Identity"—For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

"Similarity" is a further, more sophisticated measure of the relationship between two polypeptide sequences. In general, "similarity" means a comparison between the amino acids of two polypeptide chains, on a residue by residue basis, taking into account not only exact correspondences between a between pairs of residues, one from each of the sequences being compared (as for identity) but also, where there is not an exact correspondence, whether, on an evolutionary basis, one residue is a likely substitute for the other. This likelihood has an associated "score" from which the "% similarity" of the two sequences can then be determined.

Methods for comparing the identity and similarity of two or more sequences are well known in the art. Thus for instance, programs available in the Wisconsin Sequence Analysis Package, version 9.1 (Devereux J et al, Nucleic Acids Res, 12, 387–395, 1984, available from Genetics Computer Group, Madison, Wis., USA), for example the programs BESTFIT and GAP, may be used to determine the % identity between two polynucleotides and the % identity and the % similarity between two polypeptide sequences. BESTFIT uses the "local homology" algorithm of Smith and Waterman (J Mol Biol, 147, 195–197, 1981, Advances in Applied Mathematics, 2, 482–489, 1981) and finds the best single region of similarity between two sequences. BESTFIT is more suited to comparing two polynucleotide or two polypeptide sequences that are dissimilar in length, the program assuming that the shorter sequence represents a portion of the longer. In comparison, GAP aligns two sequences, finding a "maximum similarity", according to the algorithm of Neddleman and Wunsch (J Mol Biol, 48, 443–453, 1970). GAP is more suited to comparing sequences that are approximately the same length and an alignment is expected over the entire length. Preferably, the parameters "Gap Weight" and "Length Weight" used in each program are 50 and 3, for polynucleotide sequences and 12 and 4 for polypeptide sequences, respectively. Preferably, % identities and similarities are determined when the two sequences being compared are optimally aligned.

Other programs for determining identity and/or similarity between sequences are also known in the art, for instance the BLAST family of programs (Altschul S F et al, J Mol Biol, 215, 403–410, 1990, Altschul S F et al, Nucleic Acids Res., 25:389–3402, 1997, available from the National Center for Biotechnology Information (NCBI), Bethesda, Md., USA and accessible through the home page of the NCBI at www.ncbi.nlm.nih.gov) and FASTA (Pearson W R, Methods in Enzymology, 183, 63–99, 1990; Pearson W R and Lipman D J, Proc Nat Acad Sci USA, 85, 2444–2448, 1988, available as part of the Wisconsin Sequence Analysis Package).

Preferably, the BLOSUM62 amino acid substitution matrix (Henikoff S and Henikoff J G, Proc. Nat. Acad Sci. USA, 89, 10915–10919, 1992) is used in polypeptide sequence comparisons including where nucleotide sequences are first translated into amino acid sequences before comparison.

Preferably, the program BESTFIT is used to determine the % identity of a query polynucleotide or a polypeptide sequence with respect to a reference polynucleotide or a polypeptide sequence, the query and the reference sequence being optimally aligned and the parameters of the program set at the default value, as hereinbefore described.

"Identity Index" is a measure of sequence relatedness which may be used to compare a candidate sequence (polynucleotide or polypeptide) and a reference sequence. Thus, for instance, a candidate polynucleotide sequence having, for example, an Identity Index of 0.95 compared to a reference polynucleotide sequence is identical to the reference sequence except that the candidate polynucleotide sequence may include on average up to five differences per each 100 nucleotides of the reference sequence. Such differences are selected from the group consisting of at least one nucleotide deletion, substitution, including transition and transversion, or insertion. These differences may occur at the 5' or 3' terminal positions of the reference polynucleotide sequence or anywhere between these terminal positions, interspersed either individually among the nucleotides in the reference sequence or in one or more contiguous groups within the reference sequence. In other words, to obtain a polynucleotide sequence having an Identity Index of 0.95 compared to a reference polynucleotide sequence, an average of up to 5 in every 100 of the nucleotides of the in the reference sequence may be deleted, substituted or inserted, or any combination thereof, as hereinbefore described. The same applies *mutatis mutandis* for other values of the Identity Index, for instance 0.96, 0.97, 0.98 and 0.99.

Similarly, for a polypeptide, a candidate polypeptide sequence having, for example, an Identity Index of 0.95 compared to a reference polypeptide sequence is identical to the reference sequence except that the polypeptide sequence may include an average of up to five differences per each 100 amino acids of the reference sequence. Such differences are selected from the group consisting of at least one amino acid deletion, substitution, including conservative and non-conservative substitution, or insertion. These differences may occur at the amino- or carboxy-terminal positions of the reference polypeptide sequence or anywhere between these terminal positions, interspersed either individually among the amino acids in the reference sequence or in one or more contiguous groups within the reference sequence. In other words, to obtain a polypeptide sequence having an Identity Index of 0.95 compared to a reference polypeptide sequence, an average of up to 5 in every 100 of the amino acids in the reference sequence may be deleted, substituted or inserted, or any combination thereof, as hereinbefore described. The same applies *mutatis mutandis* for other values of the Identity Index, for instance 0.96, 0.97, 0.98 and 0.99.

The relationship between the number of nucleotide or amino acid differences and the Identity Index may be expressed in the following equation:

$$n_a \leq x_a - (x_a \cdot I),$$

in which:

$n_a$ is the number of nucleotide or amino acid differences, $x_a$ is the total number of nucleotides or amino acids in SEQ ID NO:1 and SEQ ID NO: 3 or SEQ ID NO:2 and SEQ ID NO: 4, respectively, I is the Identity Index, · is the symbol for the multiplication operator, and in which any non-integer product of $x_a$ and I is rounded down to the nearest integer prior to subtracting it from $x_a$.

"Homolog" is a generic term used in the art to indicate a polynucleotide or polypeptide sequence possessing a high degree of sequence relatedness to a reference sequence. Such relatedness may be quantified by determining the degree of identity and/or similarity between the two sequences as hereinbefore defined. Falling within this generic term are the terms "ortholog", and "paralog". "Ortholog" refers to a polynucleotide or polypeptide that is the functional equivalent of the polynucleotide or polypeptide in another species. "Paralog" refers to a polynucleotideor polypeptide that within the same species which is functionally similar.

"Fusion protein" refers to a protein encoded by two, unrelated, fused genes or fragments thereof. Examples have been disclosed in U.S. Pat. Nos. 5,541,087, 5,726,044. In the case of Fc-NLIBP4, employing an immunoglobulin Fc region as a part of a fusion protein is advantageous for performing the functional expression of Fc-NLIBP4 or fragments of NLIBP4, to improve pharmacokinetic properties of such a fusion protein when used for therapy and to generate a dimeric NLIBP4. The Fc-NLIBP4 DNA construct comprises in 5' to 3' direction, a secretion cassette, i.e. a signal sequence that triggers export from a mammalian cell, DNA encoding an immunoglobulin Fc region fragment, as a fusion partner, and a DNA encoding NLIBP4 or fragments thereof. In some uses it would be desirable to be able to alter the intrinsic functional properties (complement binding, Fc-Receptor binding) by mutating the functional Fc sides while leaving the rest of the fusion protein untouched or delete the Fc part completely after expression.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

What is claimed is:

1. An isolated polypeptide selected from one of the groups consisting of:
   (a) a polypeptide encoded by a polynucleotide comprising the sequence of SEQ ID NO:1 or SEQ ID NO:3;
   (b) a polypeptide comprising a polypeptide sequence comprising at least 95% identity along its entire length to the polypeptide sequence of SEQ ID NO:2 or SEQ ID NO:4;
   (c) a polypeptide comprising at least 95% identity along its entire length to the polypeptide sequence of SEQ ID NO: 2 or SEQ ID NO:4; and
   (d) the polypeptide sequence of SEQ ID NO:2 or SEQ ID NO:4.

2. The isolated polypeptide as claimed in claim 1 comprising the polypeptide sequence of SEQ ID NO: 2 or SEQ ID NO:4.

3. The isolated polypeptide as claimed in claim 1 which consists of the polypeptide sequence of SEQ ID: NO: 2.

4. The isolated polypeptide as claimed in claim 1 which consists of the polypeptide sequence of SEQ ID NO: 4.

5. The isolated polypeptide as claimed in claim 1 comprising a polypeptide sequence comprising at least 95% identity along its entire length to the polypeptide sequence of SEQ ID NO: 2.

6. The isolated polypeptide as claimed in claim 1 comprising a polypeptide sequence comprising at least 95% identity along its entire length to the polypeptide sequence of SEQ ID NO: 4.

7. The isolated polypeptide as claimed in claim 1 comprising at least 95% identity along its entire length to the polypeptide sequence of SEQ ID NO: 2.

8. The isolated polypeptide as claimed in claim 1 comprising at least 95% identity along its entire length to the polypeptide sequence of SEQ ID NO: 4.

9. The isolated polypeptide as claimed in claim 1 comprising a polypeptide sequence comprising at least 95% identity along its entire length to the polypeptide sequence of SEQ ID NO: 2.

10. The isolated polypeptide as claimed in claim 1 comprising a polypeptide sequence comprising at least 95% identity along its entire length to the polypeptide sequence of SEQ ID NO: 4.

* * * * *